(12) United States Patent
Castricini et al.

(10) Patent No.: US 11,950,791 B2
(45) Date of Patent: Apr. 9, 2024

(54) CORACOID DRILL GUIDE ASSEMBLY AND METHODS OF USE THEREOF

(71) Applicants: Smith & Nephew, Inc., Memphis, TN (US); Smith & Nephew Orthopaedics AG, Zug (CH); Smith & Nephew Asia Pacific Pte. Limited, Singapore (SG)

(72) Inventors: Roberto Castricini, Ancona (IT); Simone Bizzotto, Vigonza (IT); Alexander I. Seidl, Zurich (CH)

(73) Assignees: SMITH & NEPHEW, INC, Memphis, TN (US); SMITH & NEPHEW'ORTHOPAEDICS AG, Zug (CH); SMITH & NEPHEW ASIA PACIFIC PTE. LIMITED, Singapore (SG)

( * ) Notice: Subject to any disclaimer, the term of this patent is extended or adjusted under 35 U.S.C. 154(b) by 218 days.

(21) Appl. No.: 17/675,032

(22) Filed: Feb. 18, 2022

(65) Prior Publication Data
US 2022/0167997 A1 Jun. 2, 2022

Related U.S. Application Data

(62) Division of application No. 16/929,847, filed on Jul. 15, 2020, now Pat. No. 11,284,909.

(30) Foreign Application Priority Data

Jul. 18, 2019 (IT) .................. 102019000012318

(51) Int. Cl.
| | |
|---|---|
| A61B 17/17 | (2006.01) |
| A61B 17/16 | (2006.01) |
| A61B 17/32 | (2006.01) |

(52) U.S. Cl.
CPC .......... *A61B 17/17* (2013.01); *A61B 17/1633* (2013.01); *A61B 17/1778* (2016.11);
(Continued)

(58) Field of Classification Search
CPC ........................... A61B 17/17; A61B 17/1778
See application file for complete search history.

(56) References Cited

U.S. PATENT DOCUMENTS

| | | | | |
|---|---|---|---|---|
| 4,744,353 | A * | 5/1988 | McFarland | ........... A61F 2/0811 81/490 |
| 2011/0125160 | A1* | 5/2011 | Bagga | ................ A61B 17/1635 606/86 R |

(Continued)

FOREIGN PATENT DOCUMENTS

WO WO-2012170425 A1 * 12/2012 ......... A61B 17/1739

OTHER PUBLICATIONS

European Application No. 20186419.6-1122 Examination Report dated Mar. 2, 2022.

*Primary Examiner* — Christian A Sevilla
(74) *Attorney, Agent, or Firm* — Burns & Levinson, LLP; Joseph M. Maraia; Marlo Schepper Grolnic

(57) ABSTRACT

A coracoid drill guide assembly includes a body having a cylindrical channel on each side of the body for receiving a drill guide sleeve. The sleeves of the assembly have a 1.4 mm inner diameter to guide a 1.3 mm (or smaller) K-wire through the sleeve. An aimer arm extends from the body at a non-intersecting angle with the drill sleeve. The assembly also has a self-locking ratchet mechanism to lock the sleeve in place once the assembly has been secured to bone.

14 Claims, 9 Drawing Sheets

(52) U.S. Cl.
CPC .................... *A61B 17/1796* (2013.01); *A61B 2017/320056* (2013.01)

(56) References Cited

U.S. PATENT DOCUMENTS

2015/0359580 A1* 12/2015 Dacosta ................ A61B 17/56
606/281
2016/0089162 A1* 3/2016 Ardito ................ A61B 17/1764
606/98
2017/0014223 A1* 1/2017 Fallin ................ A61B 17/1604

* cited by examiner

CORACOID DRILL GUIDE ASSEMBLY AND METHODS OF USE THEREOF

CROSS-REFERENCE TO RELATED APPLICATIONS

This application is a divisional of co-pending U.S. application Ser. No. 16/929,847, filed Jul. 15, 2020, entitled CORACOID DRILL GUIDE ASSEMBLY AND METHODS OF USE THEREOF, which in turn claims priority to and benefit of Italian Patent Application No. 102019000012318 filed Jul. 18, 2019, the contents of which are incorporated herein by reference in their entirety for all purposes.

FIELD

The present disclosure relates generally to surgical drill guides. More specifically, the present disclosure relates to drill guide assemblies for the positioning and orienting of bone tunnels to be drilled in a coracoid bone.

BACKGROUND

The shoulder joint, also referred to as the glenohumeral joint, is the joint between the glenoid cavity (a part of the coracoid) and the head of the humerus (upper arm bone). In the case of severe bone loss in the glenoid cavity, a surgeon may perform a "Latarjet" procedure in which a surgeon secures a bone graft cut from the patient's coracoid process to a portion of the glenoid. Holes are drilled through both of the glenoid and the coracoid process through which sutures can be placed to shuttle the resected coracoid graft to the location on the glenoid. However, drilling passages at a fixed distance apart and at a fixed distance from the lateral edge of the coracoid presents challenges since the anatomy and geometry of the coracoid process varies among individuals and often has a curved shape. Misalignment of the drilled bone tunnels in the coracoid process can result in a coracoid fragment that projects from the glenoid surface, or bone tunnels that break through the lateral cortex of the coracoid process.

Drill guides for use in arthroscopic Latarjet procedures have been developed to assist the surgeon in judging where to drill passages in the coracoid process and help keep the drill steady during the drilling process. Some current coracoid drill guides use a three arm thumb puncher, including an offset sleeve through which a drill is passed to drill bone tunnels in the coracoid process. These instruments can be difficult to place in the joint and are also generally not self-locking, which can cause problems while passing the drill through the sleeve. In addition, many current coracoid drill guides are configured for use with a 2.8 mm Kirschner wire or "K-wire," which does not allow for drilling at a second location using a smaller K-wire in cases of misalignment.

SUMMARY

Described herein is a coracoid drill guide assembly which provides the ability to place a 1.3 mm (or smaller) K-wire in bone to consistently and accurately mark the placement of the bone tunnel in the coracoid process. The drill guide assembly includes a body having a cylindrical channel on each side of the body for receiving a drill guide sleeve. The sleeves of the assembly have a smaller inner diameter than current guides (i.e., 1.4 mm) to guide the 1.4 mm K-wires.

An aimer arm extends from the body at a non-intersecting angle with the drill sleeve. The assembly also has a self-locking ratchet mechanism to lock the sleeve in place once the assembly has been secured to bone. The assembly of this disclosure is advantageously smaller than current coracoid drill guides, which allows for smaller incisions to be made in the patient's skin and for the power drill used to drill the bone tunnels to be safely spaced from the patient's head.

Examples of the coracoid drill guide assembly of this disclosure may include one or more of the following, in any suitable combination.

In examples, a coracoid drill guide assembly of this disclosure includes a guide having an elongate body with a first end and a second end, and a longitudinal axis extending between the first and second ends. A proximally-facing surface and a distally-facing surface extend along the longitudinal axis between the first and second ends. The guide also includes a handle extending from the second end of the body configured to be held by a user. The guide also includes an elongate aimer arm at the first end of the body. The aimer arm extends from the distally-facing surface and is configured to be secured to a first surface of a bone. The guide also includes at least one channel at the second end of the body. The at least one channel extends transverse to the longitudinal axis from the distally-facing surface to the proximally-facing surface. The assembly also includes a sleeve slidably disposed within the at least one channel such that the sleeve extends at a non-intersecting angle relative to the aimer arm. A distal end of the sleeve is configured to be secured to a second surface of the bone. The sleeve has a bore extending from a proximal end to a distal end of the sleeve for the passage of a guidewire. An outer diameter of a distal portion of the sleeve selected to be smaller than an outer diameter of a proximal portion of the sleeve. The guide also includes a locking mechanism for locking the sleeve at a predetermined position within the at least one channel.

In further examples, a distal end of the aimer arm comprises a hooked end for securing to the first surface of the bone. In examples, the locking mechanism includes a pawl insertable through an opening in the first end of the body adjacent to the at least one channel. The pawl is selectively engageable with a rack on a surface of the proximal portion of the sleeve for the locking the sleeve at the predetermined position. In examples, the at least one channel is two channels extending on opposing sides of the aimer arm. A distance between the two channels is about 10 mm. In examples, the outer diameter of the proximal portion of the sleeve is about 6.5 mm and the outer diameter of the distal portion of the sleeve is about 4.0 mm. In examples, a diameter of the bore is about 1.4 mm. In examples, the distal end of the sleeve has a pointed tip. In examples, the proximal end of the sleeve includes a depth stop. A diameter of the depth stop is selected to be larger than a diameter of the channel for limiting distal movement of the sleeve within the channel. In examples, the aimer arm is formed integrally with the body.

Examples of a method for positioning a bone tunnel in bone of this disclosure include positioning a distal tip of an aimer arm of a drill guide against a second bone surface. A drill sleeve is advanced through a channel of the drill guide such that the sleeve extends at a non-intersecting angle relative to the aimer arm, whereby the bone is fixed between the distal tip of the aimer arm and a distal tip of the drill sleeve. A guidewire is inserted through a bore of the drill sleeve and drilled through the bone. The drill guide is removed from the bone while leaving the guidewire in place to locate a bone tunnel. A cannulated drill is then passed over the guidewire and used to drill the bone tunnel.

In further examples, the guidewire is a 1.3 mm K-wire and a diameter of the bore is about 1.4 mm. In examples, an outer diameter of a distal portion of the sleeve is selected to be smaller than an outer diameter of a proximal portion of the sleeve. In examples, the outer diameter of the distal portion of the sleeve is about 4.0 mm and the outer diameter of the proximal portion of the sleeve is about 6.5 mm. Examples of the method further include locking the sleeve within the channel at a preselected position with a locking mechanism. In examples, the drill is a 2.7 mm drill.

Examples of a coracoid drill kit of this disclosure include a guide having an elongate body with a first end and a second end, and a longitudinal axis extending between the first and second ends. A proximally-facing surface and a distally-facing surface extend along the longitudinal axis between the first and second ends. The guide also includes a handle extending from the second end of the body configured to be held by a user. The guide also includes an elongate aimer arm at the first end of the body, the aimer arm extending from the distally-facing surface and configured to be secured to a first surface of a bone. The guide also includes at least one channel at the second end of the body. The at least one channel extends transverse to the longitudinal axis from the distally-facing surface to the proximally-facing surface. The kit also includes at least one sleeve for slidably disposing within the at least one channel such that the sleeve extends at a non-intersecting angle relative to the aimer arm. An outer diameter of a distal portion of the sleeve is selected to be smaller than an outer diameter of a proximal portion of the sleeve. The kit also includes at least one guidewire for insertion through a bore of the at least one sleeve. The kit also includes a cannulated drill for disposing over the at least one guidewire. In examples, the guidewire is a 1.3 mm K-wire and the drill is a 2.7 mm drill. In examples, the guide further includes a locking mechanism for locking the sleeve at a predetermined position within the at least one channel.

These and other features and advantages will be apparent from a reading of the following detailed description and a review of the associated drawings. It is to be understood that both the foregoing general description and the following detailed description are explanatory only and are not restrictive of aspects as claimed.

BRIEF DESCRIPTION OF THE DRAWINGS

The disclosure will be more fully understood by reference to the detailed description, in conjunction with the following figures, wherein.

DETAILED DESCRIPTION

Figure 1A:
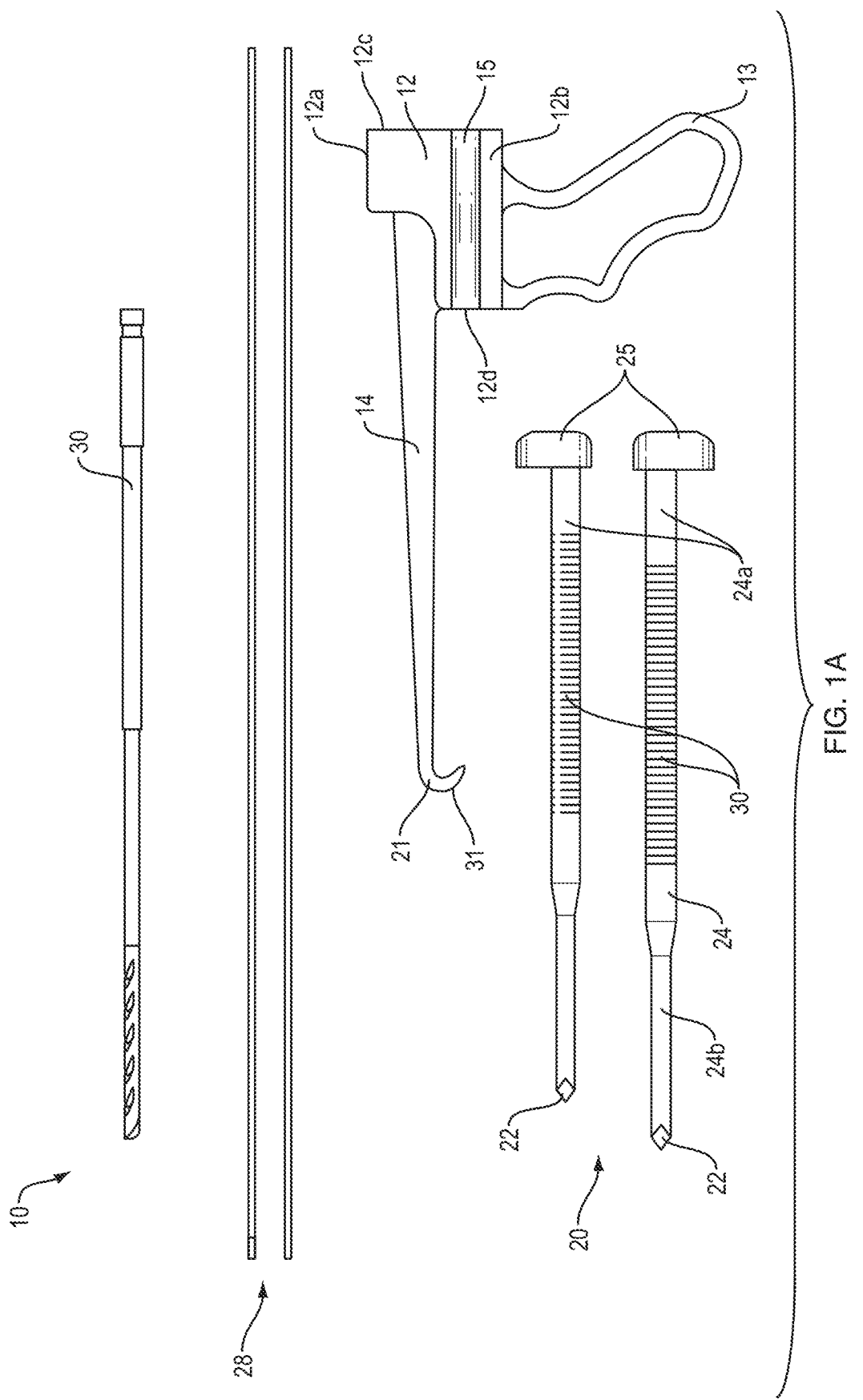
FIGS. 1A and 1B are examples of a coracoid drill guide assembly of this disclosure in a disassembled view (FIG. 1A) and an assembled view (FIG. 1B)

In the description that follows, like components have been given the same reference numerals, regardless of whether they are shown in different examples. To illustrate example (s) in a clear and concise manner, the drawings may not necessarily be to scale and certain features may be shown in somewhat schematic form. Features that are described and/or illustrated with respect to one example may be used in the same way or in a similar way in one or more other examples and/or in combination with or instead of the features of the other examples.

As used in the specification and claims, for the purposes of describing and defining the invention, the terms "about" and "substantially" are used to represent the inherent degree of uncertainty that may be attributed to any quantitative comparison, value, measurement, or other representation. The terms "about" and "substantially" are also used herein to represent the degree by which a quantitative representation may vary from a stated reference without resulting in a change in the basic function of the subject matter at issue. "Comprise," "include," and/or plural forms of each are open ended and include the listed parts and can include additional parts that are not listed. "And/or" is open-ended and includes one or more of the listed parts and combinations of the listed parts. Use of the terms "upper," "lower," "below," and the like is intended only to help in the clear description of the present disclosure and are not intended to limit the structure, positioning and/or operation of the disclosure in any manner.

Figure 1B:
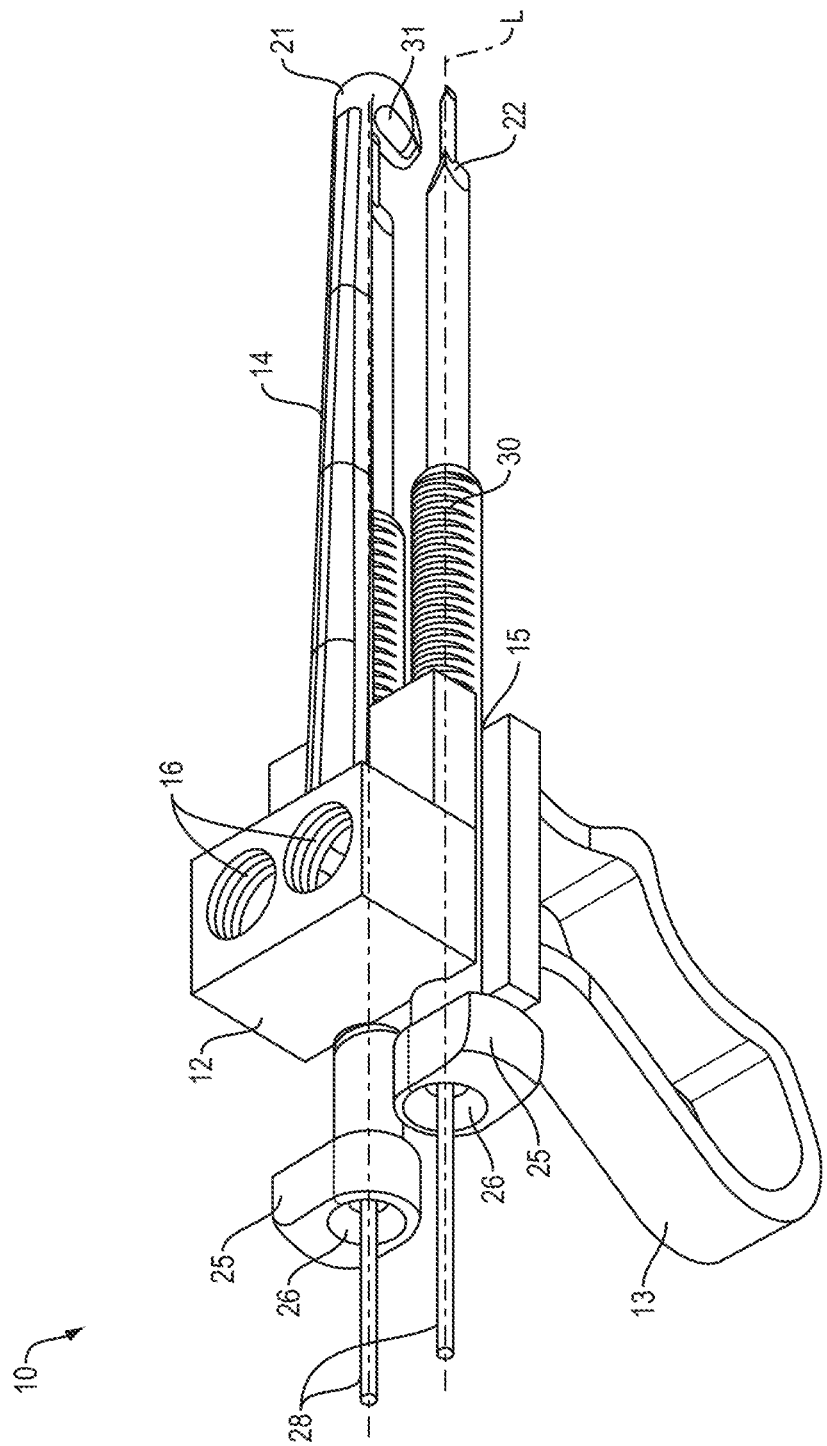

Referring now to FIGS. 1A and 1B, a coracoid drill guide drill guide assembly 10 of this disclosure is shown in a disassembled view (FIG. 1A) and an assembled view (FIG. 1B). The drill guide assembly 10 includes a guide body 12 having an upper first end 12a and a lower second end 12b. A proximally facing surface 12c and a distally-facing surface 12d extend between the first end 12a and the second end 12b of the guide body 12. A handle 13 extends below the second end 12b of the guide body 12 and is configured to be held by a user in a "pistol-style" configuration. In alternative examples, not shown, the handle 13 is an in-line handle, formed substantially coaxially with the guide body 12. An elongate aimer arm 14 is formed integrally with and extends from the distally facing surface 12d of the guide body 12. The aimer arm includes a distal tip 21 with a spiked hook 31 which is configured to contact a bone surface. In alternative examples, not shown, the distal tip 21 could be pointed or comprise a blunted end, such as a spherical tip. In yet further examples, not shown, the aimer arm 14 could be adjustable relative to the handle 13 to help facilitate access to different surgical sites. The guide body 12 further includes at least one cylindrical channel 15 extending from the proximally facing surface 12c to the distally facing surface 12d for slidably receiving an elongate drill sleeve 20. When assembled, the aimer arm 14 extends from the guide body 12 at a non-intersecting angle with a longitudinal axis L of the drill sleeve 20. In the example of FIGS. 1A and 1B, two channels 15 are defined on opposite sides of the guide body 12 configured for positioning two parallel bone tunnels through the bone. In examples, a distance between the channels 15 is about 10 mm, ensuring accurate and consistent placement of the bone tunnels about 10 mm apart within the bone.

Still referring to FIGS. 1A and 1B, the drill sleeve 20 includes an elongated sleeve body 24 having a distal tip 22 and a depth stop 25 at a proximal end of the drill sleeve 20. The distal tip 22 is sharp and pointed to provide a stable engagement with a bone surface. The depth stop 25 can be used by a surgeon to grasp and manipulate the drill sleeve 20 during surgery. The depth stop 25 has a larger outer diameter than that of the channel 15, such that when drill sleeve 20 is inserted through the channel 15, the depth stop 25 prevents drill sleeve 20 from being inserted completely through the channel 15. A diameter of a proximal portion 24a of the sleeve body 24 is selected to be larger than a diameter of a distal portion 24b of the sleeve body. For example, the diameter of the proximal portion 24a of the sleeve body 24 may be about 6.4 mm while a diameter of the distal portion 24b of the sleeve body 24 may be about 4.0 mm. The sleeve body 24 has a cylindrical bore 26 extending through the sleeve body 24 which provides a passageway for a guidewire 28. In examples, a diameter of the bore 26 may be about 1.4 mm to allow passage of a 1.3 mm (or smaller) K-wire. When assembled, a distance between the center of the guidewire 28 and the inner side of the aimer arm 14 is selected be to about 6 mm, thus providing a fixed offset of the bone tunnels from the edge of the bone to prevent fragmenting or breaking of the bone. The drill sleeve 20 is configured to direct the guidewire 28 into a bone surface to locate the bone tunnel. In addition, the drill sleeve 20 supports the guidewire 28 to prevent it from being deflected by the hard bone surface. The first end 12a of the guide body 12 also includes at least one threaded opening 16 for receiving a threaded ratchet pawl 23 (FIG. 2A) located adjacent to the channel 15. The proximal portion 24a of the sleeve body 24 also includes a rack 30 in the form of a series of ratchet teeth or radial grooves along one side of sleeve body 24. The ratchet pawl 23 of the handle 13 is configured to engage with the rack 30 and lock the drill sleeve 20 in a desired position within channel 15.

The initial steps of an example of a Latarjet procedure, which includes the use of drill guide assembly 10, will now be described with reference to FIGS. 2A-E. The Latarjet procedure described below advantageously uses fewer portals compared to current Latarjet procedures. The Latarjet procedure also advantageously uses two pairs of round buttons as an alternative to the commonly-used screw fixation or the use of a single button. In examples, the procedure is performed with the patient in a "beach chair" position with or without traction.

Figure 2A:
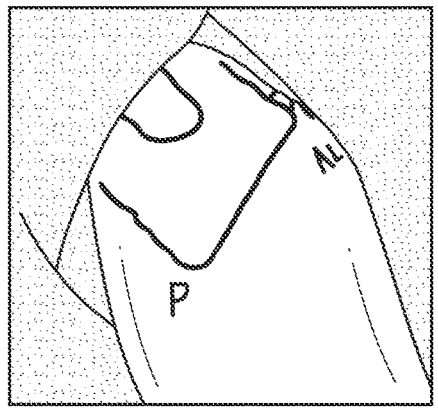
FIGS. 2A-E illustrate the initial steps of an example of a Latarjet procedure.
Figure 2A:

As shown in FIG. 2A, six portals in the shoulder joint are used in the procedure: Posterior (P), Antero-Superior (AS), Antero-Lateral (AL), Antero-Inferior (AI), Axillary or Inferior (AX), and superior of the Coracoid (C). An arthroscope (not shown) is introduced through the posterior portal (P). From the AS portal, a coblation wand is introduced to remove the labrum. An anterior capsulectomy is then performed until the fibers of the subscapularis are exposed.

Figure 2B:
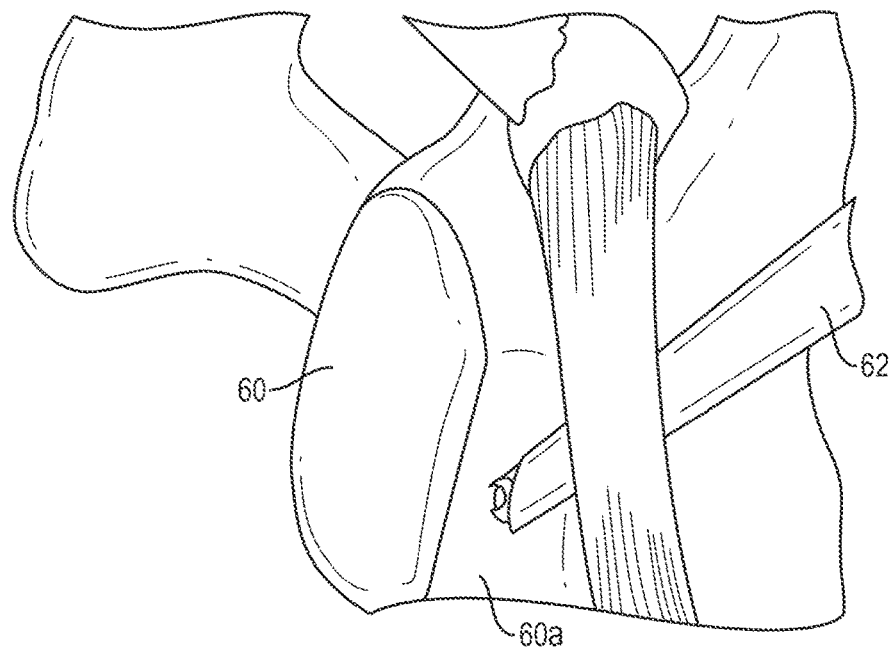
Figure 3A:
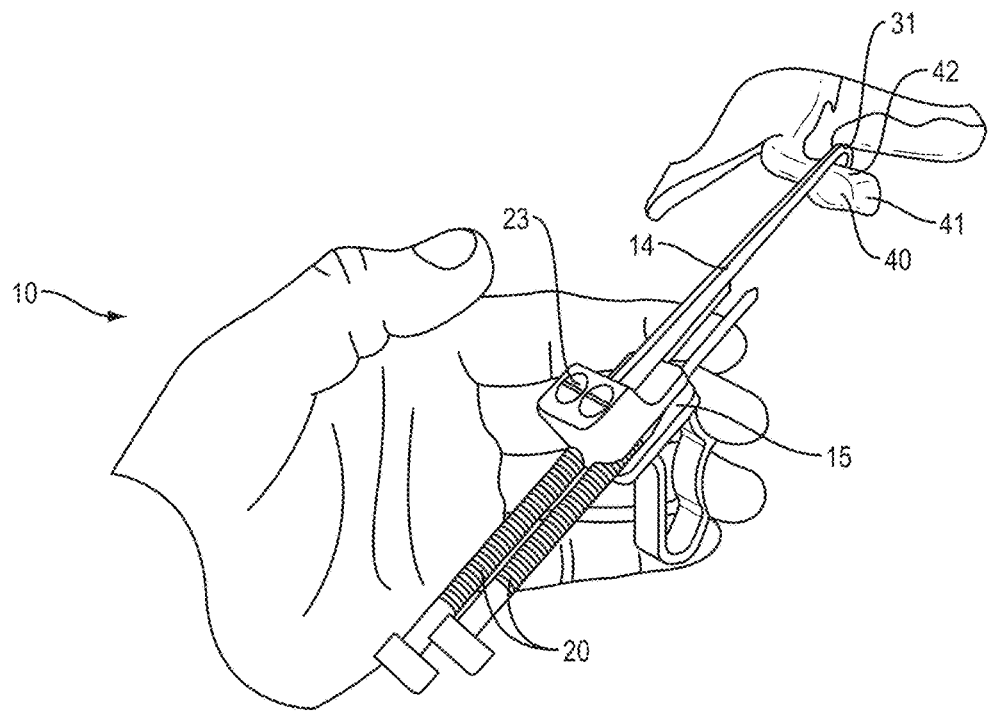
FIGS. 3A-F illustrate the use of the coracoid drill guide assembly of FIGS. 1A and 1B in drilling bone tunnels in a coracoid process during the Latarjet procedure.

As shown in FIG. 2B, the anterior rim 60a of the glenoid 60 is decorticated with an arthroscopic burr 62 to create a flat and bleeding bony surface to accommodate attachment of the graft. The anterior interval is then opened and the coraco-acromial ligament is released to expose the coracoid process 40 (FIG. 3A). The antero-lateral (AL) portal is then prepared parallel to the superior border of the Subscapularis in the direction of the coracoid base.

Figure 2C:
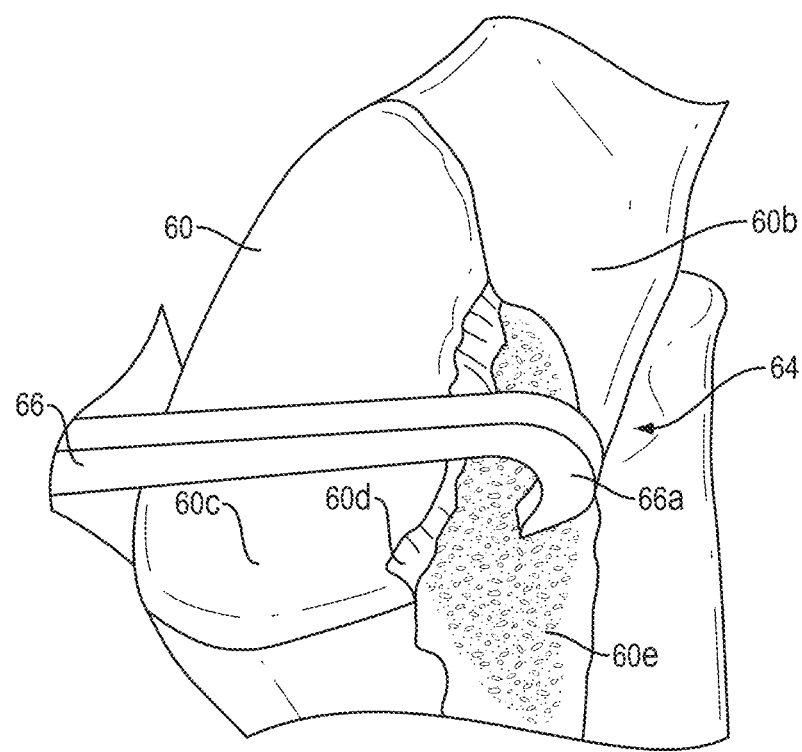

As shown in FIG. 2C, a glenoid drill guide 64 is used to ensure the correct position of two drilled tunnels, which are preferably parallel to each other and perpendicular to the glenoid neck 60b. In order to find the correct position of the glenoid drill guide 64, the arthroscope is placed in the AL portal. A needle (not shown) is then inserted from posterior to anterior (for example, using the posterior portal (P)) parallel to the glenoid surface 60c and in the middle of the anterior glenoid bone defect below the mid-line. The hook 66a of the arm 66 of the glenoid drill guide 64 is inserted through the posterior portal (P) and introduced parallel to the glenoid surface 60c to minimize damage to the articular cartilage. Once sufficiently advanced, the glenoid drill guide 64 is rotated to engage the anterior edge 60d of the glenoid 60 with the hook 66a. Preferably, the hook 66a is centered on the glenoid defect with the tip of the hook 66a on the glenoid rim 60e, for example, between the 3 and 4 o'clock position. The arm 66 of the glenoid drill guide 64 is preferably parallel to and flush with the glenoid surface 60c.

Figure 2D:
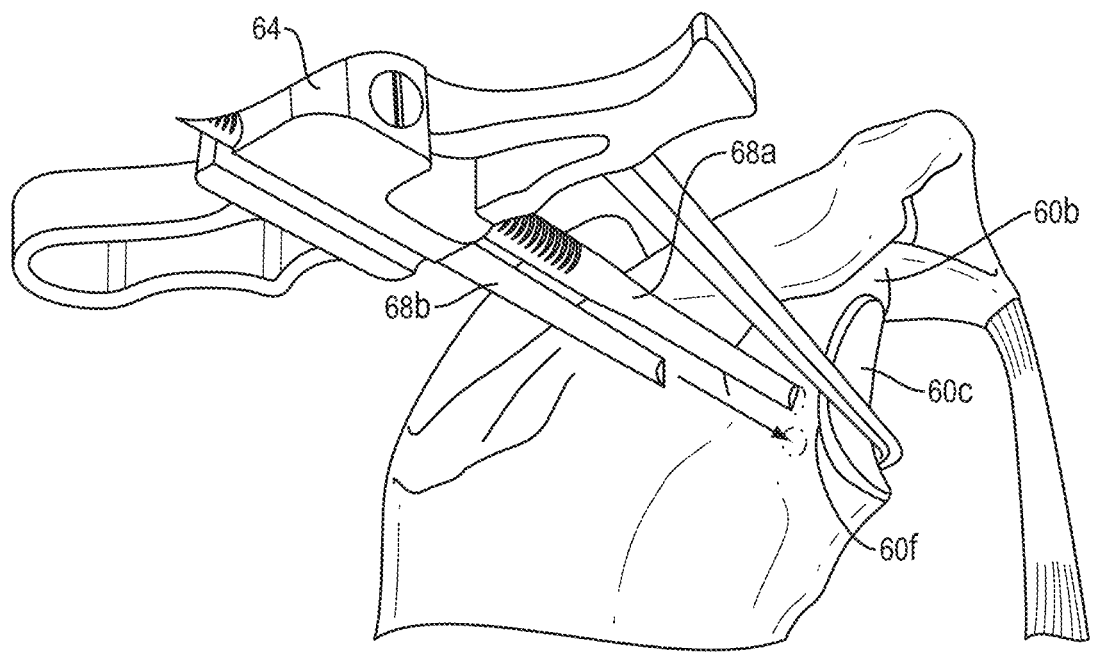

As shown in FIG. 2D, the glenoid drill guide 64 is secured with two bullets 68a, 68b introduced percutaneously. Specifically, a skin incision is created and a first bullet 68a is advanced until it is firmly in contact with the posterior aspect of the glenoid neck 60b. The step is repeated for the second bullet 68b. Once in position, the two bullets 68a, 68b remain against the posterior aspect of the glenoid neck 60b. A drill (for example, a 2.8 mm sleeved drill) (not shown) is introduced through each bullet 68a, 68b and advanced under power until the bullets 68a, 68b exit from the anterior aspect of the glenoid 60, creating two bone tunnels through the glenoid 60. Preferably, the two resulting bone tunnels are 5 mm below the cortical edge 60f of the glenoid surface 60c, parallel to each other and 10 mm apart.

Figure 2E:
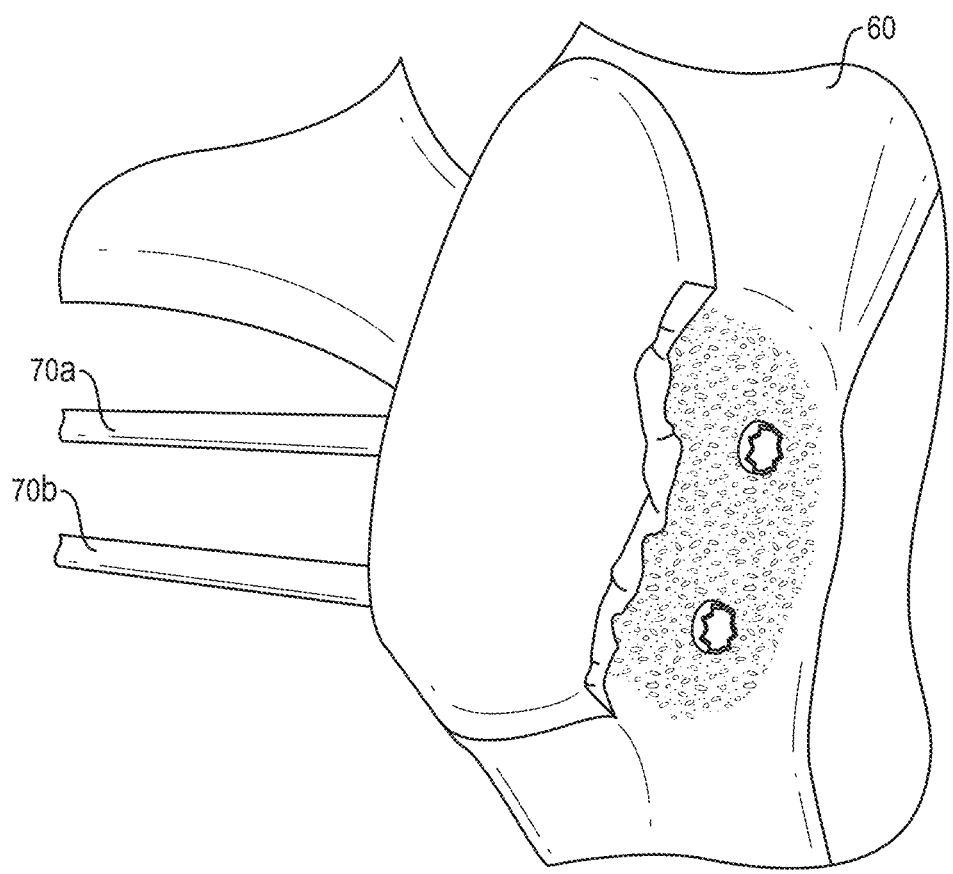

As shown in FIG. 2E, the inner drill is removed from the glenoid 60, leaving the cannulated outer sleeves 70a, 70b in place. The drill sleeves 70a, 70b are used to create an accessible pilot hole through the glenoid 60 and to complete the remaining procedural steps, including shuttling guide wires for coracoid transfer and final fixation of the coracoid graft on the glenoid 60. The arthroscope is then introduced from the Antero Lateral portal (AL) and the intra- and extra-articular space is controlled by a Subscapularis spreader (not shown). The spreader is introduced in a closed configuration from the posterior portal and is gently pushed against the subscapularis muscle. From the Antero-Inferior portal (AI), the split of the subscapularis is performed with the coblation wand.

The use of drill guide assembly 10 of this disclosure will now be described with reference to FIGS. 3A-F in positioning bone tunnels in a bone prior to attachment of a bone graft to the bone in the Latarjet procedure. In examples, the bone is a coracoid process 40 of the shoulder joint. The coracoid process 40 may be initially prepared for the procedure by rasping the inferior surface of the coracoid process 40 for better attachment of the bone graft. Specifically, in examples, the arthroscope is placed through the Anterior-Inferior (AI) portal and the coblation wand is placed through the Axillary portal (AX). The coracoid and the conjoint tendon are isolated. Through the Axillary portal (AX), the pectoralis minor is released from the medial side. The arthroscope is introduced through the Antero-Inferior portal (AI), while a rasp is introduced through the Antero-Lateral portal (AI). The under surface of the coracoid process 40 is abraded to create a flat surface.

Figure 3B:
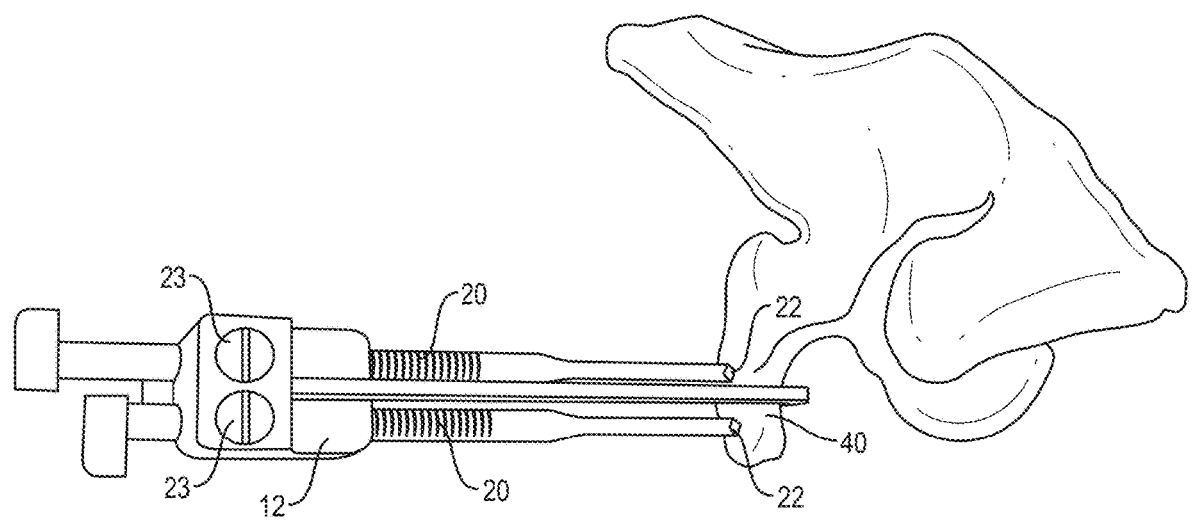

As shown in FIG. 3A, the drill guide assembly 10 of this disclosure is introduced into the patient's shoulder from the Superior portal (C). The surgeon adjusts the orientation of aimer arm 14 until the aimer arm 14 is placed at the lateral edge 42 of the coracoid process 40 and the hook 31 is placed on the inferior surface of the coracoid process 40 to hold the aimer arm 14 in place. In examples, the hook 31 is placed about 1 cm from the coracoid tip 41. As shown in FIG. 3B, the drill sleeve 20 is inserted through channel 15 of the guide 10 so that the distal tip 22 is flush against the anterior surface of the coracoid process 40. In examples, the drill sleeve 20 is inserted perpendicular to the lateral edge 42 of the coracoid process 40 and at a 90° angle with respect to the anterior surface. The drill sleeve 20 is then locked into the channel 15 by the ratchet pawl 23.

Figure 3C:
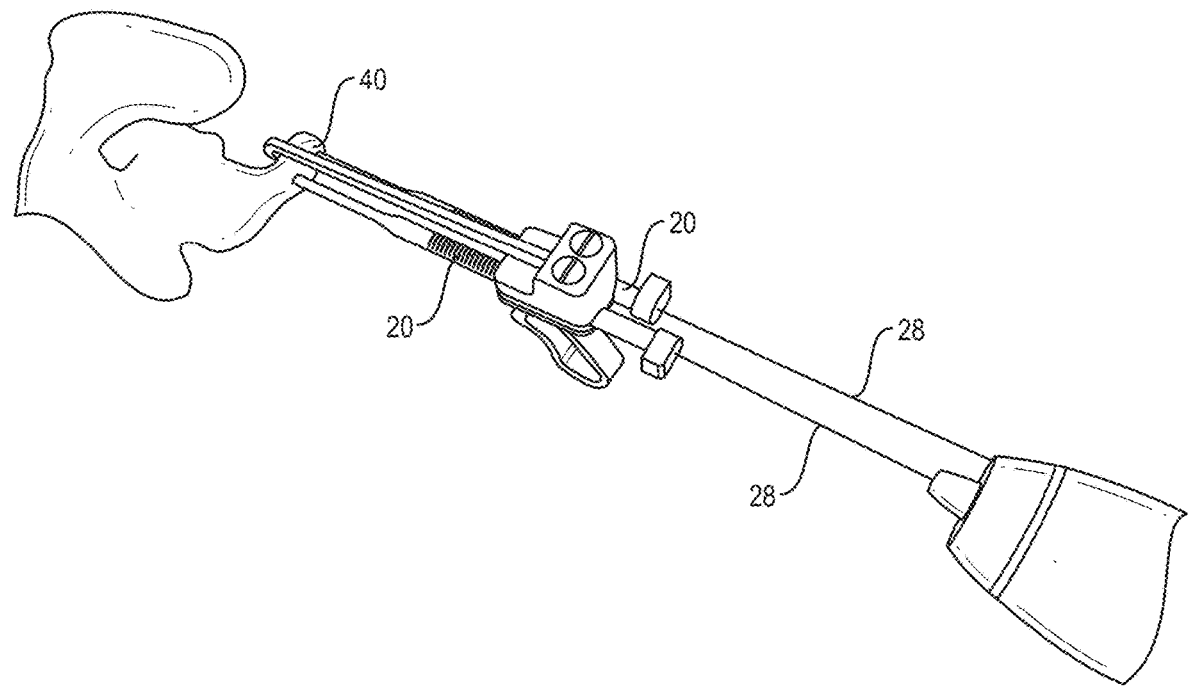
Figure 3D:
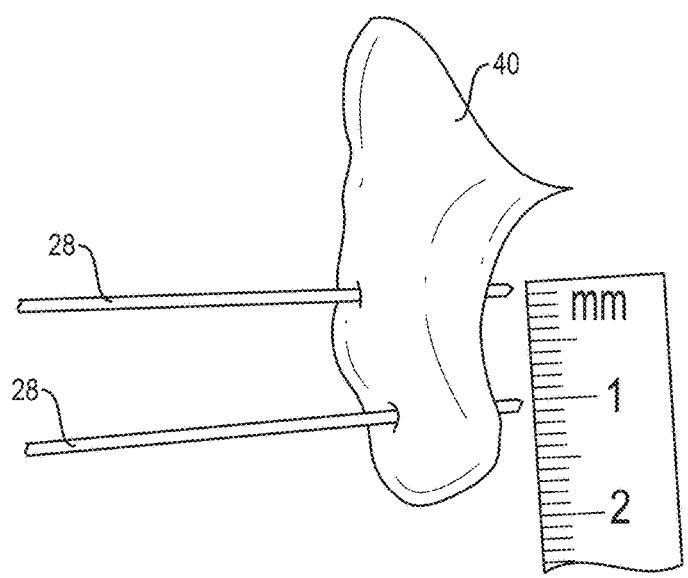
Figure 3E:
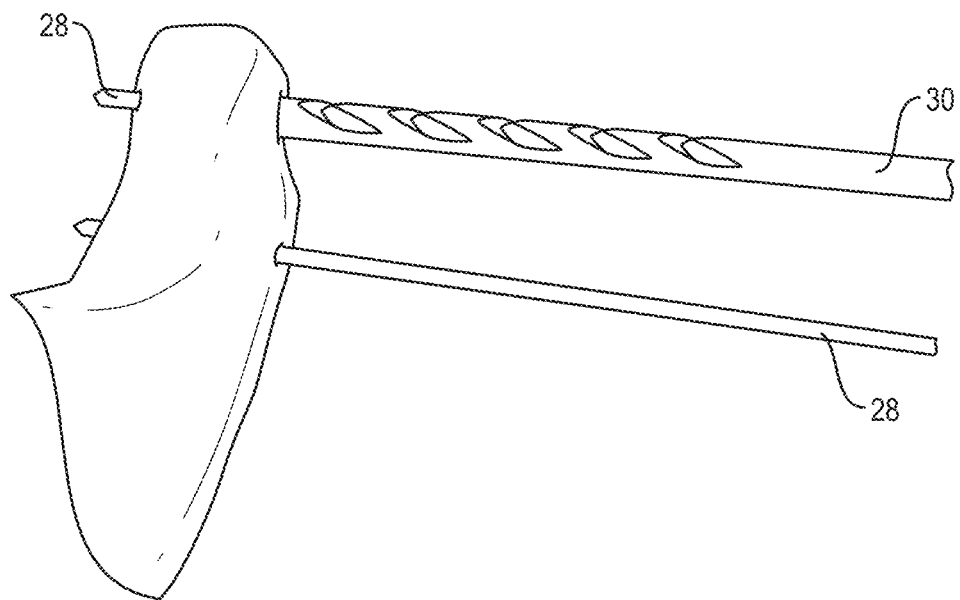
Figure 3F:
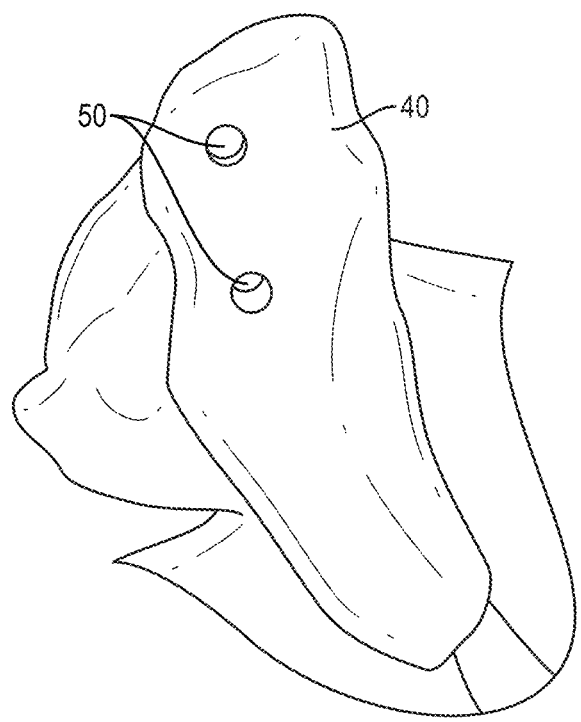

Subsequently, and as shown in FIG. 3C, a guidewire 28 (for example, a 1.14 mm or 1.3 mm K-wire) is inserted through drill sleeve 20 and drilled through the coracoid process 40. As shown in FIG. 3D, the drill guide assembly 10 is then removed from the patient's shoulder, leaving the guidewire 28 in place. In the case where two guidewires 28 are drilled through the coracoid process 40, a distance of 10 mm is confirmed between the guidewires 28. As shown in FIG. 3E, a cannulated drill 30 (for example, a 2.7 mm drill), is placed over the guidewire 28 for drilling the bone tunnels 50. The guidewires 28 are then removed, leaving the bone tunnels 50 in the coracoid process 40 (FIG. 3F) for subsequent securing of the bone graft. It is also contemplated by this disclosure that, rather than using a drill sleeve 20 sized for the passage of the guidewire 28, the drill sleeve 20 could be sized for passage of the drill 30, to reduce completion time of the procedure.

The final steps of the example of the Latarjet procedure will now be described. In examples, a suture retriever loaded with a high-strength suture is loaded in the inferior glenoid tunnel from posterior. The suture is pushed with the suture retriever and retrieved from anterior. An additional suture retriever is inserted into the coracoid process. This step is performed for both the glenoid and coracoid holes, making sure not to tangle the sutures. With the arthroscope in Antero-Inferior (AI) portal, a reciprocating saw is used through the Antero-Lateral portal to perform the osteotomy of the coracoid process 40, creating the coracoid graft. With the arthroscope in Antero-Lateral (AL) portal, the coracoid graft is passed through the subscapularis split, making sure to open the subscapularis with the Subscapularis spreader and pulling on the sutures posteriorly. The coracoid graft is manipulated with a switching stick until the surface of the graft is flush with the anterior surface of the glenoid neck 60b. Preferably, the surgeon will check that the posterior sutures are sliding into the glenoid 60 and the coracoid process 40. In examples, a blue/white suture loop is carefully cut to separate the white suture bundle into two parts. Each bundle is pulled through a hole of a fixation device (for example, a round button) using the suture retriever from the previous step.

Figure 4:
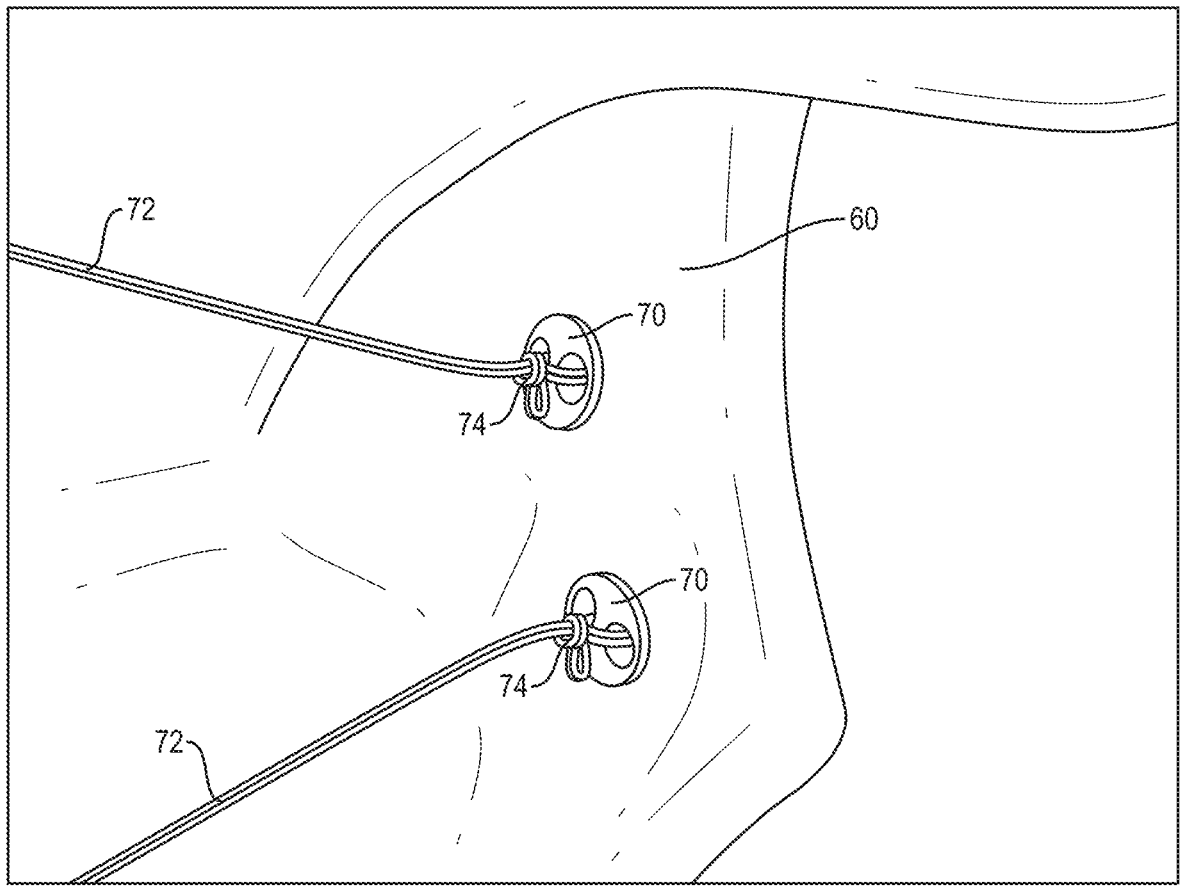
FIG. 4 illustrates a final step in the Latarjet procedure.

As shown in FIG. 4, the fixation device 70 is advanced down the white suture bundle 72 and a Nice Knot (i.e., a sliding locking knot) 74 is tied until it the fixation device 70 sits flush against the posterior face of the glenoid 60. A suture tensioner is advanced through the posterior portal (P) and tension is applied tension of up to 100 Newton. Simultaneously, the position of the coracoid graft (not shown) is preferably checked under visualization. For example, a finger or probe is used to check the stability and positioning of the coracoid graft. Once the graft has been tensioned, the posterior sliding knots 74 are further secured with half-hitch knots.

One skilled in the art will realize the disclosure may be embodied in other specific forms without departing from the spirit or essential characteristics thereof. The foregoing examples are therefore to be considered in all respects illustrative rather than limiting of the disclosure described herein. Scope of the disclosure is thus indicated by the appended claims, rather than by the foregoing description, and all changes that come within the meaning and range of equivalency of the claims are therefore intended to be embraced therein.

What is claimed is:

1. A method for positioning a bone tunnel in bone comprising:
   positioning a distal tip of an aimer arm of a drill guide against a surface of the bone, the drill guide further comprising:
   an elongate body having a first end and a second end, and a longitudinal axis extending between the first and second ends, a proximally-facing surface and a distally-facing surface extending along the longitudinal axis between the first and second ends; and
   the aimer arm positioned at the first end of the body, the aimer arm extending from the distally-facing surface, the aimer arm comprising a lateral surface, a medial surface, and a tip such that a width between the lateral surface and medial surface tapers from the distally-facing surface towards the tip;
   advancing a drill sleeve through at least one channel of the drill guide such that the drill sleeve extends at a parallel angle relative to the medial surface of the aimer arm, whereby the bone is fixed between the distal tip of the aimer arm and a distal tip of the drill sleeve;
   inserting a guidewire through a bore of the drill sleeve and drilling through the bone with the guidewire;
   removing the drill guide from the bone while leaving the guidewire in place to locate a bone tunnel;
   passing a cannulated drill over the guidewire; and
   drilling the bone tunnel with the cannulated drill.

2. The method of claim 1, wherein the guidewire is a 1.3 mm K-wire.

3. The method of claim 1, wherein a diameter of the bore is about 1.4 mm.

4. The method of claim 1, wherein an outer diameter of a distal portion of the drill sleeve is selected to be smaller than an outer diameter of a proximal portion of the drill sleeve.

5. The method of claim 1, wherein an outer diameter of a distal portion of the drill sleeve is about 4.0 mm and an outer diameter of a proximal portion of the drill sleeve is about 6.5 mm.

6. The method of claim 1, further comprising locking the drill sleeve within the at least one channel at a preselected position with a locking mechanism.

7. The method of claim 6, wherein the locking mechanism comprises a pawl insertable through an opening in the first end of the body adjacent to the at least one channel, the pawl selectively engageable with a rack on a surface of a proximal portion of the drill sleeve for the locking the drill sleeve at the predetermined position.

8. The method of claim 1, wherein the drill is a 2.7 mm drill.

9. The method of claim 1, wherein a distal end of the aimer arm comprises a hooked end for securing to the surface of the bone.

10. The method of claim 1, wherein the at least one channel is two channels extending on opposing sides of the aimer arm, and wherein a distance between the two channels is about 10 mm.

11. The method of claim 1, wherein the tip of the drill sleeve is pointed.

12. The method of claim 1, wherein a proximal end of the drill sleeve comprises a depth stop, a diameter of the depth stop selected to be larger than a diameter of the channel for limiting distal movement of the drill sleeve within the channel.

13. The method of claim 1, wherein the aimer arm is formed integrally with the body.

14. The method of claim 1, wherein the bone is a glenoid bone.

* * * * *